US005635594A

United States Patent [19]

Lehrer et al.

[11] Patent Number: 5,635,594

[45] Date of Patent: Jun. 3, 1997

[54] GALLINACINS - ANTIBIOTIC PEPTIDES

[75] Inventors: Robert I. Lehrer, Santa Monica; Vladimir N. Kokryakov, Los Angeles; Sylvia S. L. Harwig, Woodland Hills, all of Calif.

[73] Assignee: University of California, Los Angeles, Los Angeles, Calif.

[21] Appl. No.: 212,236

[22] Filed: Mar. 11, 1994

[51] Int. Cl.$^6$ ....................... C07K 14/435; C07K 14/465; A61K 38/17

[52] U.S. Cl. .......................... 530/317; 530/321; 530/324; 530/827; 530/830

[58] Field of Search ................................ 435/69.1; 514/2, 514/12, 21; 530/324, 317, 829, 321, 827, 830

[56] References Cited

U.S. PATENT DOCUMENTS

| | | | |
|---|---|---|---|
| 4,543,252 | 9/1985 | Lehrer et al. | 514/12 |
| 4,659,692 | 4/1987 | Lehrer et al. | 514/12 |
| 4,705,777 | 11/1987 | Lehrer et al. | 514/12 |

OTHER PUBLICATIONS

Evans, E.W. et al. *J. Leukocyte Biology* 56:661–665 (1994).

Nakamura et al., Tachyplesin, a Class of Antimicorbial Peptide from the Hemocytes of the Horshoe Crab (*Tachupleus tridentatus*), J. Biol. Chem. (1988) 263:16709–16713.

Miyata et al., Antimicrobial Peptides, Isolated from Horseshoe Crab Hemocytes, Tachyplesin II, and Polyphemusins I and II: Chemical Structures and Biological Activity, J. Biochem; (1989) 106:663–668.

Murakami et al., Direct Virus Inactivation of Tachyplesin I and Its Isopeptides from Horseshoe Crab Hemocytes, Chemotherapy (1991) 37:327–334.

Morimoto et al., Inhibitory Effect of Tachyplesin I on the Proliferation of Human Immunodeficiency Virus in vitro, Chemotherapy (1991) 37:206–211.

Nakashima et al., Anti–Human Immunodeficiency Virus of a Novel Synthetic Peptide, T22 ([Tyr–5,12, Lys–7]Polyphemusin II): a Possible Inhibitor of Virus–Cell Fusion, Antimicrobial Agents and Chemotherapy (1992) 1249–1255.

Lehrer et al., Direct Inactivation of Viruses by MCP–1 an MCP–2 Natural Peptide Antibiotics from Rabbit Leukocytes; J. Virol. (1985) 54:467–472.

Kokryakov et al., Protegrins: leukocyte antimicrobial peptides that combine features of corticostatic defensins adn tachyplesins; FEBS (1993) 337:231–236.

Mirgorodskaya, et al., Primary structure of three cationic peptides from porcine neutrophils; FEBS (1993) 330:339–342.

Storici, et al., A Novel cDNA Sequence Encoding a Pih Leukocyte Antimicrobial Peptide with a Cathelin–like Pro–sequence; Biochem. Biophys. Res. Comm. (1993) 196:1363–1367.

Lehrer, R.I. et al., Defensins: Endogenous Antibiotic Peptides of Animal Cells, Cell (1991) 64:229–230.

Lehrer, R.I. et al., Defensins: Antimicrobial and Cytotoxic Peptides of Mammalian Cells, Ann Rev Immunol (1993) 11:105–128.

Selsted, M.E. et al., Purification, Primary Structures, and Antibacterial Activities of β–Defensins, a New Family of Antimicrobial Peptides from Bovine Neutrophils; J Biol Chem (1993) 268:6641–6648.

Tang, Y–Q., Characterization of the Disulfide Motif in BNBD–12, an Antimicrobial β–Defensin Peptide from Bovine Neutrophils; J Biol Chem (1993) 268:6649–6653.

Diamond, G. et al., Tracheal antimicrobial peptide, a cysteine–rich peptide from mammalian tracheal mucosa: Peptide isolation and cloning of a cDNA; Proc Natl Acad Sci (USA) (1991) 88:3952–3958.

Diamond, G. et al., Airway epithelial cells are the site of expression of a mammalian antimicrobial peptide gene; Proc Natl Acad Sci USA (1993) 90:4596–4600.

(List continued on next page.)

*Primary Examiner*—Dian C. Jacobson

*Attorney, Agent, or Firm*—Morrison & Foerster LLP

[57] ABSTRACT

Peptide-based compounds containing six invariant cysteine residues are useful as preservatives and in preventing, treating, or ameliorating microbial infection in animals and plants. These compounds are of the formulas:

1 2 3 4 5 6 7 8 9 10
G—$B_2$—$B_3$—S—(D/E)—C—F—$B_8$—$B_9$—(N/S)—
11 12 13 14 15 16 17 18 19 20
G—F—C—(G/A/S)—F—(V/L/I)—$B_{17}$—C—P—(Y/S)—
21 22 23 24 25 26 27
(V/L/I)—T—(V/L/I)—(V/L/I)—(G/A/S)—G—$B_{27}$—
28 29 30 31 32 33 34 35 36
C—(G/A/S)—$B_{30}$—F—(H/Y)—(V/L/I)—C—C—$B_{36}$—
37 38 39
$B_{37}$—I—W (SEQ ID NO: 1) (1)

and 1 2 3 4 5 6 7 8 9
(V/L/I)—F—C—$B_4$—(G/S/A)—G—(G/S/A)—C—H—
10 11 12 13 14 15 16 17
F—(G/S/A)—(G/S/A)—C—P—S—H—(V/L/I)—
18 19 20 21 22 23 24
(V/L/I)—$B_{19}$—(V/L/I)—G—(G/S/A)—C—F—
25 26 27 28 29 30 31 32 33 34
(G/S/A)—F—$B_{27}$—(G/S/A)—C—C—$B_{31}$—W—P—W—
35 36
(Q/N)—(G/S/A) (SEQ ID NO: 2) (2)

wherein each $B_i$ is a basic amino acid and the N-terminal acylated and/or C-terminal amidated or esterified forms thereof, either in optionally —SH stabilized linear or in cystine-bridged form.

9 Claims, 10 Drawing Sheets

OTHER PUBLICATIONS

Lambert et al., Insect Immunity: Isolation from immune blood of the dipteran *Phormia terranovae* of two insect antibacterial peptides with sequence homology to rabbit lung macrophage bactericidal peptides, Proc. Natl. Acad. Sci. (USA) (1989) 88:262–265.

Broekaert et al., Antimicrobial Peptides from *Amaranthus caudatus* Seeds with Sequence Homology tothe Cysteine/Glycine–Rich Domain o Chitin–Binding Proteins, Biochemistry (1992) 31:4308–4314.

Cornelissen et al., Strategies for Control of Fungal Disease with Transgenic Plants, Plant Physiol (1993) 101:709–712.

Haln et al., Disease resistance results from foreign phytoalexin expression in a novel plant, Nature (1993) 361:153–156.

| | | 1 | | 10 | | | | | | 20 | | | | 30 | | |
|---|---|---|---|---|---|---|---|---|---|---|---|---|---|---|---|---|
| Gal 1α | | GRKSD | C | FRKN | G | F | C | AFLK | CP | YLTLIS | G | K | C | SRFHL- | CC | KRIW |
| Gal 1 | | GRKSD | C | FRKS | G | F | C | AFLK | CP | SLTLIS | G | K | C | SRFYL- | CC | KRIW |
| Gal 2 | | LF | C | --KG | G | S | C | HFGG | CP | SHLIKV | G | S | C | FGFRS- | CC | KWPWNA |
| TAP | | NPVS | C | VRNK | G | I | C | VPIR | CP | GSMKQI | G | T | C | VGRAVK | CC | RKK |
| BNBD1 | | DFAS | C | HTNG | G | I | C | LPNR | CP | GHMIQI | G | I | C | FRPRVK | CC | RSW |
| BNBD2 | V | RNHVT | C | RINR | G | F | C | VPIR | CP | GRTRQI | G | T | C | FGPRIK | CC | RSW |
| BNBD5 | pEVV | RNPQS | C | RWNM | G | V | C | IPIS | CP | GNMRQI | G | T | C | FGPRIK | CC | RSW |
| BNBD10 | pEGV | RSYLS | C | WGNR | G | I | C | LLNR | CP | GRNRQI | G | T | C | LAPRVK | CC | R |
| BNBD11 | | GPLS | C | RRNG | G | V | C | IPIR | CP | GPNRQI | G | T | C | FGRPVK | CC | RSW |

FIG. 1

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 2
( D ) OTHER INFORMATION: /note= "This position is B which is a basic amino acid."

( i x ) FEATURE:
( A ) NAME/KEY: Modified-site
( B ) LOCATION: 3
( D ) OTHER INFORMATION: /note= "This position is B which is a basic amino acid."

( i x ) FEATURE:
( A ) NAME/KEY: Modified-site
( B ) LOCATION: 5
( D ) OTHER INFORMATION: /note= "This position is D/E."

( i x ) FEATURE:
( A ) NAME/KEY: Modified-site
( B ) LOCATION: 8
( D ) OTHER INFORMATION: /note= "This position is B which is a basic amino acid."

( i x ) FEATURE:
( A ) NAME/KEY: Modified-site
( B ) LOCATION: 9
( D ) OTHER INFORMATION: /note= "This position is B which is a basic amino acid."

( i x ) FEATURE:
( A ) NAME/KEY: Modified-site
( B ) LOCATION: 10
( D ) OTHER INFORMATION: /note= "This position is N/S."

( i x ) FEATURE:
( A ) NAME/KEY: Modified-site
( B ) LOCATION: 14
( D ) OTHER INFORMATION: /note= "This position is G/A/S."

( i x ) FEATURE:
( A ) NAME/KEY: Modified-site
( B ) LOCATION: 16
( D ) OTHER INFORMATION: /note= "This position is V/L/I."

( i x ) FEATURE:
( A ) NAME/KEY: Modified-site
( B ) LOCATION: 17
( D ) OTHER INFORMATION: /note= "This position is B which is a basic amino acid."

( i x ) FEATURE:
( A ) NAME/KEY: Modified-site
( B ) LOCATION: 20
( D ) OTHER INFORMATION: /note= "This position is Y/S."

-continued ( i x ) FEATURE:
( A ) NAME/KEY: Modified-site
( B ) LOCATION: 21
( D ) OTHER INFORMATION: /note= "This position is V/L/I."

( i x ) FEATURE:
( A ) NAME/KEY: Modified-site
( B ) LOCATION: 23
( D ) OTHER INFORMATION: /note= "This position is V/L/I."

( i x ) FEATURE:
( A ) NAME/KEY: Modified-site
( B ) LOCATION: 24
( D ) OTHER INFORMATION: /note= "This position is V/L/I."

( i x ) FEATURE:
( A ) NAME/KEY: Modified-site
( B ) LOCATION: 25
( D ) OTHER INFORMATION: /note= "This position is G/A/S."

( i x ) FEATURE:
( A ) NAME/KEY: Modified-site
( B ) LOCATION: 27
( D ) OTHER INFORMATION: /note= "This position is B which is a basic amino acid."

( i x ) FEATURE:
( A ) NAME/KEY: Modified-site
( B ) LOCATION: 29
( D ) OTHER INFORMATION: /note= "This position is G/A/S."

( i x ) FEATURE:
( A ) NAME/KEY: Modified-site
( B ) LOCATION: 30
( D ) OTHER INFORMATION: /note= "This position is B which is a basic amino acid."

( i x ) FEATURE:
( A ) NAME/KEY: Modified-site
( B ) LOCATION: 32
( D ) OTHER INFORMATION: /note= "This position is H/Y."

( i x ) FEATURE:
( A ) NAME/KEY: Modified-site
( B ) LOCATION: 33
( D ) OTHER INFORMATION: /note= "This position is V/L/I."

( i x ) FEATURE:
( A ) NAME/KEY: Modified-site
( B ) LOCATION: 36
( D ) OTHER INFORMATION: /note= "This position is B which is a basic amino acid."

( i x ) FEATURE:
( A ) NAME/KEY: Modified-site
( B ) LOCATION: 37
( D ) OTHER INFORMATION: /note= "This position is B which is a basic amino acid."

( x i ) SEQUENCE DESCRIPTION: SEQ ID NO:1:

```
Gly Xaa Xaa Ser Xaa Cys Phe Xaa Xaa Xaa Gly Phe Cys Xaa Phe Xaa
1               5                   10                  15

Xaa Cys Pro Xaa Xaa Thr Xaa Xaa Xaa Gly Xaa Cys Xaa Xaa Phe Xaa
            20                  25                  30

Xaa Cys Cys Xaa Xaa Ile Trp
        35
```

( 2 ) INFORMATION FOR SEQ ID NO:2:

( i ) SEQUENCE CHARACTERISTICS:
( A ) LENGTH: 36 amino acids
( B ) TYPE: amino acid
( C ) STRANDEDNESS: single
( D ) TOPOLOGY: linear -continued ( i x ) FEATURE:
( A ) NAME/KEY: Modified-site
( B ) LOCATION: 1
( D ) OTHER INFORMATION: /note= "This position is V/L/I."

( i x ) FEATURE:
( A ) NAME/KEY: Modified-site
( B ) LOCATION: 4
( D ) OTHER INFORMATION: /note= "This position is B which is a basic amino acid."

( i x ) FEATURE:
( A ) NAME/KEY: Modified-site
( B ) LOCATION: 5
( D ) OTHER INFORMATION: /note= "This position is G/S/A."

( i x ) FEATURE:
( A ) NAME/KEY: Modified-site
( B ) LOCATION: 7
( D ) OTHER INFORMATION: /note= "This position is G/S/A."

( i x ) FEATURE:
( A ) NAME/KEY: Modified-site
( B ) LOCATION: 11
( D ) OTHER INFORMATION: /note= "This position is G/S/A."

( i x ) FEATURE:
( A ) NAME/KEY: Modified-site
( B ) LOCATION: 12
( D ) OTHER INFORMATION: /note= "This position is G/S/A."

( i x ) FEATURE:
( A ) NAME/KEY: Modified-site
( B ) LOCATION: 17
( D ) OTHER INFORMATION: /note= "This position is V/L/I."

( i x ) FEATURE:
( A ) NAME/KEY: Modified-site
( B ) LOCATION: 18
( D ) OTHER INFORMATION: /note= "This position is V/L/I."

( i x ) FEATURE:
( A ) NAME/KEY: Modified-site
( B ) LOCATION: 19
( D ) OTHER INFORMATION: /note= "This position is B which is a basic amino acid."

( i x ) FEATURE:
( A ) NAME/KEY: Modified-site
( B ) LOCATION: 20
( D ) OTHER INFORMATION: /note= "This position is V/L/I."

( i x ) FEATURE:
( A ) NAME/KEY: Modified-site
( B ) LOCATION: 22
( D ) OTHER INFORMATION: /note= "This position is G/S/A."

( i x ) FEATURE:
( A ) NAME/KEY: Modified-site
( B ) LOCATION: 25
( D ) OTHER INFORMATION: /note= "This position is G/S/A."

( i x ) FEATURE:
( A ) NAME/KEY: Modified-site
( B ) LOCATION: 27
( D ) OTHER INFORMATION: /note= "This position is B which is a basic amino acid."

( i x ) FEATURE:
( A ) NAME/KEY: Modified-site
( B ) LOCATION: 28
( D ) OTHER INFORMATION: /note= "This position is G/S/A."

( i x ) FEATURE:
( A ) NAME/KEY: Modified-site
( B ) LOCATION: 31
( D ) OTHER INFORMATION: /note= "This position is B which is a basic amino acid."

( i x ) FEATURE:

-continued ( A ) NAME/KEY: Modified-site
( B ) LOCATION: 35
( D ) OTHER INFORMATION: /note= "This position is Q/N."

( i x ) FEATURE:
( A ) NAME/KEY: Modified-site
( B ) LOCATION: 36
( D ) OTHER INFORMATION: /note= "This position is G/S/A."

( x i ) SEQUENCE DESCRIPTION: SEQ ID NO:2:

Xaa Phe Cys Xaa Xaa Gly Xaa Cys His Phe Xaa Xaa Cys Pro Ser His
1 5 10 15

Xaa Xaa Xaa Xaa Gly Xaa Cys Phe Xaa Phe Xaa Xaa Cys Cys Xaa Trp
20 25 30

Pro Trp Xaa Xaa
35

( 2 ) INFORMATION FOR SEQ ID NO:3:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( x i ) SEQUENCE DESCRIPTION: SEQ ID NO:3:

Gly Arg Lys Ser Asp Cys Phe Arg Lys Asn Gly Phe Cys Ala Phe Leu
1 5 10 15

Lys Cys Pro Tyr Leu Thr Leu Ile Ser Gly Lys Cys Ser Arg Phe His
20 25 30

Leu Cys Cys Lys Arg Ile Trp
35

( 2 ) INFORMATION FOR SEQ ID NO:4:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( x i ) SEQUENCE DESCRIPTION: SEQ ID NO:4:

Gly Arg Lys Ser Asp Cys Phe Arg Lys Ser Gly Phe Cys Ala Phe Leu
1 5 10 15

Lys Cys Pro Ser Leu Thr Leu Ile Ser Gly Lys Cys Ser Arg Phe Tyr
20 25 30

Leu Cys Cys Lys Arg Ile Trp
35

( 2 ) INFORMATION FOR SEQ ID NO:5:

( i ) SEQUENCE CHARACTERISTICS:
( A ) LENGTH: 36 amino acids
( B ) TYPE: amino acid
( C ) STRANDEDNESS: single
( D ) TOPOLOGY: linear ( x i ) SEQUENCE DESCRIPTION: SEQ ID NO:5:

Leu Phe Cys Lys Gly Gly Ser Cys His Phe Gly Gly Cys Pro Ser His
1 5 10 15

Leu Ile Lys Val Gly Ser Cys Phe Gly Phe Arg Ser Cys Cys Lys Trp
20 25 30

Pro Trp Asn Ala
35

( 2 ) INFORMATION FOR SEQ ID NO:6:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( x i ) SEQUENCE DESCRIPTION: SEQ ID NO:6:

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35
```

( 2 ) INFORMATION FOR SEQ ID NO:7:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( x i ) SEQUENCE DESCRIPTION: SEQ ID NO:7:

```
Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35
```

( 2 ) INFORMATION FOR SEQ ID NO:8:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( x i ) SEQUENCE DESCRIPTION: SEQ ID NO:8:

```
Arg Asn His Val Thr Cys Arg Ile Asn Arg Gly Phe Cys Val Pro Ile
1               5                   10                  15

Arg Cys Pro Gly Arg Thr Arg Gln Ile Gly Thr Cys Phe Gly Pro Arg
            20                  25                  30

Ile Lys Cys Cys Arg Ser Trp
        35
```

( 2 ) INFORMATION FOR SEQ ID NO:9:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( x i ) SEQUENCE DESCRIPTION: SEQ ID NO:9:

```
Arg Asn Pro Gln Ser Cys Arg Trp Asn Met Gly Val Cys Ile Pro Ile
1               5                   10                  15

Ser Cys Pro Gly Asn Met Arg Gln Ile Gly Thr Cys Phe Gly Pro Arg
            20                  25                  30

Ile Lys Cys Cys Arg Ser Trp
        35
```

-continued ( 2 ) INFORMATION FOR SEQ ID NO:10:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( x i ) SEQUENCE DESCRIPTION: SEQ ID NO:10:

Arg Ser Tyr Leu Ser Cys Trp Gly Asn Arg Gly Ile Cys Leu Leu Asn
1 5 10 15

Arg Cys Pro Gly Arg Asn Arg Gln Ile Gly Thr Cys Leu Ala Pro Arg
20 25 30

Val Lys Cys Cys Arg
35

( 2 ) INFORMATION FOR SEQ ID NO:11:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( x i ) SEQUENCE DESCRIPTION: SEQ ID NO:11:

Gly Pro Leu Ser Cys Arg Arg Asn Gly Gly Val Cys Ile Pro Ile Arg
1 5 10 15

Cys Pro Gly Pro Asn Arg Gln Ile Gly Thr Cys Phe Gly Arg Pro Val
20 25 30

Lys Cys Cys Arg Ser Trp
35

GALLINACINS - ANTIBIOTIC PEPTIDES

This invention was made with funding from NIH Grant No. A122839. The. U.S. Government has certain rights in this invention.

TECHNICAL FIELD

The invention relates to the field of antibiotic peptides. In particular, the invention concerns peptides, some of which are isolated from chicken neutrophils, that have a wide range of antimicrobial activities.

BACKGROUND ART

One of the defense mechanisms against infection by both animals and plants is the production of peptides that have antimicrobial and antiviral activity. Various classes of these peptides have been isolated from tissues both of plants and animals. One well known class of such peptides is the tachyplesins which were first isolated from the hemocytes of the horseshoe crab as described by Nakamura, T. et al. *J Biol Chem* (1988) 263:16709–16713. This article described the initial tachyplesin isolated from the Japanese species, Tachyplesin I, which is a 17-amino acid amidated peptide containing four cysteine residues providing two intramolecular cystine bonds. In a later article by this group, Miyata, T. et al. *J Biochem* (1989) 106:663–668, extends the studies to the American horseshoe crab and isolated a second tachyplesin, Tachyplesin II, consisting of 17 residues amidated at the C-terminus, also containing four cysteine residues and two intramolecular disulfide bonds. Two additional 18-mers, called polyphemusins, highly homologous to Tachyplesin II and containing the same positions for the four cysteine residues, were also isolated. Polyphemusin I and Polyphemusin II differ from each other only in the replacement of one arginine residue by a lysine. All of the peptides were described as having antifungal and antibacterial activity. A later article by Murakami, T. et al. *Chemotherapy* (1991) 37:327–334, describes the antiviral activity of the tachyplesins with respect to vesicular stomatus virus; Herpes Simplex Virus I & II, Adenovirus I, Reovirus II and Poliovirus I were resistant to inactivation by Tachyplesin I. Morimoto, M. et al. *Chemotherapy* (1991) 37:206–211, found that Tachyplesin I was inhibitory to Human Immunodeficiency Virus. This anti-HIV activity was found also to be possessed by a synthetic analog of Polyphemusin II as described by Nakashima, H. et al. *Antimicrobial Agents and Chemotherapy* (1992) 1249–1255. Antiviral peptides have also been found in rabbit leukocytes as reported by Lehrer, R. I. et al. *J Virol* (1985) 54:467–472.

Another class of antimicrobial and antiviral peptides, the "protegrins" have been isolated from porcine leukocytes as reported by the present applicants in a paper by Kokryakov, V. N. et al. *FEBS* (1993) 337:231–236. An additional paper disclosing cationic peptides from porcine neutrophils was published by Mirgorodskaya, O. A. et al. *FEBS* (1993) 330:339–342. Storici, P. et al. *Biochem Biophys Res Comm* (1993) 196:1363–1367, report the recovery of a DNA sequence which encodes a pig leukocyte antimicrobial peptide with a cathelin-like prosequence and is reported to be one of the protegrins.

Other important classes of cysteine-containing antimicrobial peptides include the defensins, β-defensins and insect defensins. The defensins are somewhat longer peptides characterized by six invariant cysteines and three intramolecular cystine disulfide bonds. Defensins were described by Lehrer, R. I. et al. *Cell* (1991) 64:229–230; Lehrer, R. I. et al. *Ann Rev Immunol* (1993) 11:105–128. A review of mammalian-derived defensins by Lehrer, R. I. et al. is found in *Annual Review Immunol* (1993) 11:105–128; three patents have issued on the defensins: U.S. Pat. Nos. 4,705,777; 4,659,692; and U.S. Pat. No. 4,543,252. Defensins have been found in the polymorphonucleated neutrophils (PMN) of humans and of several other animals, as well as in rabbit pulmonary alveolar macrophages, and in murine small intestinal epithelial (Paneth) cells and in corresponding cells in humans.

β-Defensins are found in bovine neutrophils and respiratory epithelial cells. See Selsted, M. E. et al. *J Biol Chem* (1993) 288:6641–6648, Tang, Y-Q. *J Biol Chem* (1993) 268:6649–6653, and Diamond, G. et al. *Proc Natl Acad Sci* (USA) (1991) 88:3952–3958, Diamond, G. et al. *Proc Natl Acad Sci* USA (1993) 90:4596–4600. Insect defensins have been reported by Lambert, J. et al. *Proc Natl Acad Sci* (USA) (1989) 88:262–265.

Antifungal and antibacterial peptides and proteins have also been found in plants (Broekaert, W. F. et al. *Biochemistry* (1992) 31:4308–4314) as reviewed by Cornelissen, B. J. C. et al. *Plant Physiol* (1993) 101:709–712. Expression systems for the production of such peptides have been used to transform plants to protect the plants against such infection as described, for example, by Haln, R. et al. *Nature* (1993) 361:153–156.

The present invention relates to an additional group of antimicrobial peptides with broad spectrum activity, representative members of which can be isolated from chicken neutrophils. These peptides, named gallinacins, contain six cysteine residues in a pattern reminiscent of the β-defensins and the tracheal antibiotic peptide (TAP) derived from bovine respiratory epithelial cells. These peptides contain 35–40 amino acids and are useful as preservatives and therapeutics.

DISCLOSURE OF THE INVENTION

The invention is directed to gallinacins, i.e., peptides of about 35–40 amino acid residues characterized by six invariant cysteines and either by a characteristic pattern of basic, acidic and neutral amino acids and/or being isolatable from leukocytes of *Gallus gallus* using the method of the invention. These peptides can be produced synthetically and some can be produced recombinantly or can be isolated from their native sources and purified for use as preservatives or in pharmaceutical compositions in treating or preventing infection in animals. Alternatively, the peptides can be formulated into compositions which can be applied to plants to protect them against viral or microbial infection. In still another approach, the DNA encoding the peptides can be expressed in situ, in animals or preferably in plants, to combat infections. The peptides are also useful as standards in antimicrobial assays and in binding endotoxins.

Accordingly, in one aspect, the invention is directed to peptides of the formulas:

1 2 3 4 5 6 7 8 9 10
G—$B_2$—$B_3$—S—(D/E)—C—F—$B_8$—$B_9$—(N/S)—
11 12 13 14 15 16 17 18 19 20
G—F—C—(G/A/S)—F—(V/L/I)—$B_{17}$—C—P—(Y/S)—
21 22 23 24 25 26 27
(V/L/I)—T—(V/L/I)—(V/L/I)—(G/A/S)—G—$B_{27}$—
28 29 30 31 32 33 34 35 36
C—(G/A/S)—$B_{30}$—F—(H/Y)—(V/L/I)—C—C—$B_{36}$—
37 38 39
$B_{37}$—I—W (SEQ ID NO: 1) (1)

and 1 2 3 4 5 6 7 8 9
(V/L/I)—F—C—$B_4$—(G/S/A)—G—(G/S/A)—C—H—
10 11 12 13 14 15 16 17
F—(G/S/A)—(G/S/A)—C—P—S—H—(V/L/I)—
18 19 20 21 22 23 24
(V/L/I)—$B_{19}$—(V/L/I)—G—(G/S/A)—C—F—
25 26 27 28 29 30 31 32 33 34
(G/S/A)—F—$B_{27}$—(G/S/A)—C—C—$B_{31}$—W—P—W—
35 36
(Q/N)—(G/S/A) (SEQ ID NO: 2) (2)

wherein each $B_i$ independently is a basic amino acid; and the C-terminal amidated or esterified and/or N-terminal acylated forms thereof, including the optionally SH-stabilized linear and the cyclic forms thereof, with the proviso that those compounds of formulas (1) and (2) of the formulas Gal 1α GRKSDCFRKNGFCAFLKCPYLTLISGKCSRFHLCCKRIW (SEQ ID NO: 3)

Gal 1 GRKSDCFRKS GFCAFLKCPSLTLISGKCSRFYLCCKRIW (SEQ ID NO: 4)

and

Gal 2 LFCKGGSCHFGGCPSHLIKVGSCFGFRSCCKWPWNA (SEQ ID NO: 5)

in the cyclic and free amino and free acid forms must be in purified and isolated form.

In another aspect, the invention comprises a purified and isolated peptide of the formula:

1 2 3 4 5 6 7 8 9 10
G—$B_2$—$B_3$—S—(D/E)—C—F—$B_8$—$B_9$—(N/S)—
11 12 13 14 15 16 17 18 19 20
G—F—C—(G/A/S)—F—(V/L/I)—$B_{17}$—C—P—(Y/S)—
21 22 23 24 25 26 27
(V/L/I)—T—(V/L/I)—(V/L/I)—(G/A/S)—G—$B_{27}$—
28 29 30 31 32 33 34 35 36
C—(G/A/S)—$B_{30}$—F—(H/Y)—(V/L/I)—C—C—$B_{36}$—
37 38 39
$B_{37}$—I—W (SEQ ID NO: 1) (1)

and

-continued 1 2 3 4 5 6 7 8 9
(V/L/I)—F—C—$B_4$—(G/S/A)—G—(G/S/A)—C—H—
10 11 12 13 14 15 16 17
F—(G/S/A)—(G/S/A)—C—P—S—H—(V/L/I)—
18 19 20 21 22 23 24
(V/L/I)—$B_{19}$—(V/L/I)—G—(G/S/A)—C—F—
25 26 27 28 29 30 31 32 33 34
(G/S/A)—F—$B_{27}$—(G/S/A)—C—C—$B_{31}$—W—P—W—
35 36
(Q/N)—(G/S/A) (SEQ ID NO: 2) (2)

wherein each $B_i$ is independently a basic amino acid; and the amidated or esterified and/or N-terminal acylated forms thereof, including the optionally SH-stabilized linear and the cyclic forms thereof which peptides are isolatable from arian leukocytes by the methods similar to those described herein.

In still other aspects, the invention is directed to recombinant materials useful for the production of the peptides of the invention as well as plants or animals modified to contain expression systems for the production of these peptides. The invention is also directed to pharmaceutical compositions and compositions for application to plants containing the peptides of the invention as active ingredients or compositions which contain expression systems for production of the peptides or for in situ expression of the nucleotide sequence encoding these peptides. The invention is also directed to methods to prepare the invention peptides synthetically, to antibodies specific for these peptides, and to the use of the peptides as preservatives.

In other aspects, the invention is directed to the use of the compounds of the invention as standards in antimicrobial assays. The invention is also directed to use of the invention compounds as preservatives for foods or other perishables.

BRIEF DESCRIPTION OF THE DRAWINGS

FIG. 1 (SEQ ID NO. 3 through SEQ ID NO. 11) shows the amino acid sequences of Gal1, Gal1α and Gal2 as compared with peptides of the β-defensin class.

MODES OF CARRYING OUT THE INVENTION

Figure 2:
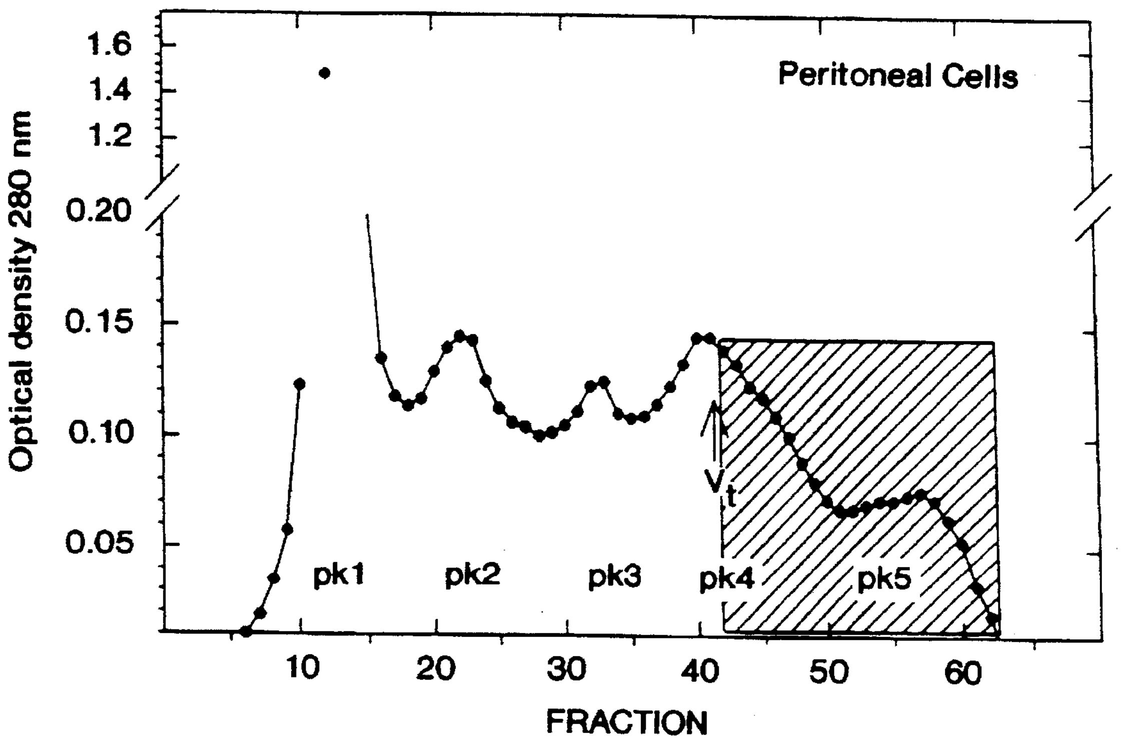
FIG. 2 shows the elution pattern of a concentrate of the ultrafiltrate of chicken neutrophils applied to an Acrilex P10 column.

The peptides of the invention are described by the formulas:

1 2 3 4 5 6 7 8 9 10
G—$B_2$—$B_3$—S—(D/E)—C—F—$B_8$—$B_9$—(N/S)—
11 12 13 14 15 16 17 18 19 20
G—F—C—(G/A/S)—F—(V/L/I)—$B_{17}$—C—P—(Y/S)—
21 22 23 24 25 26 27
(V/L/I)—T—(V/L/I)—(V/L/I)—(G/A/S)—G—$B_{27}$—
28 29 30 31 32 33 34 35 36
C—(G/A/S)—$B_{30}$—F—(H/Y)—(V/L/I)—C—C—$B_{36}$—
37 38 39
$B_{37}$—I—W (SEQ ID NO: 1) (1)

and 1 2 3 4 5 6 7 8 9
(V/L/I)—F—C—$B_4$—(G/S/A)—G—(G/S/A)—C—H—
10 11 12 13 14 15 16 17
F—(G/S/A)—(G/S/A)—C—P—S—H—(V/L/I)—
18 19 20 21 22 23 24
(V/L/I)—$B_{19}$—(V/L/I)—G—(G/S/A)—C—F—
25 26 27 28 29 30 31 32 33 34
(G/S/A)—F—$B_{27}$—(G/S/A)—C—C—$B_{31}$—W—P—W—
35 36
(Q/N)—(G/S/A) (SEQ ID NO: 2) (2)

Those peptides which occur in nature must be in purified and isolated form.

The designation $B_i$ in each case represents a basic amino acid at the specified position in the peptide. The peptides of the invention may optionally be extended by 1–10, preferably only 1–5 and more preferably 1–3 noninterfering amino acids at either the N-terminus or C-terminus or both.

The amino terminus of the peptide may be in the free amino form or may be acylated by a group of the formula RCO—, wherein R represents a hydrocarbyl group of 1-6C. The hydrocarbyl group is saturated or unsaturated and is typically, for example, methyl, ethyl, i-propyl, t-butyl, n-pentyl, cyclohexyl, cyclohexen-2-yl, hexen-3-yl, hexyn-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1-6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The peptides of the invention may be in straight-chain or cyclic form. The straight-chain forms are convertible to the cyclic forms, and vice versa. Methods for forming disulfide bonds to create the cyclic peptides are well known in the art, as are methods to reduce disulfides to form the linear compounds. The linear compounds can be stabilized by addition of a suitable alkylating agent such as iodoacetamide.

The cyclic forms are the result of the formation of cystine linkages among all or some of the six invariant cysteine residues. Cyclic forms of the invention include all possible permutations of cystine bond formation; if the cysteines are numbered in order of their occurrence starting at the N-terminus as $C_1$, $C_2$, $C_3$, $C_4$, $C_5$ and $C_6$, these permutations include, for example,

| | | |
|---|---|---|
| $C_1$-$C_2$; | | |
| $C_1$-$C_4$; | | |
| $C_1$-$C_6$; | | |
| $C_2$-$C_3$; | | |
| $C_2$-$C_6$; | | |
| $C_3$-$C_5$; | $C_4$-$C_6$; | |
| $C_1$-$C_2$, | $C_3$-$C_4$; | |
| $C_1$-$C_3$, | $C_2$-$C_4$; | |
| $C_1$-$C_4$, | $C_2$-$C_3$; | |
| $C_1$-$C_2$, | $C_3$-$C_4$, | $C_5$-$C_6$; |
| $C_1$-$C_3$, | $C_2$-$C_4$, | $C_5$-$C_6$; |
| $C_1$-$C_5$, | $C_2$-$C_4$, | $C_3$-$C_6$; |

and the like.

As the linearized forms of the native cyclic peptides have valuable activities, even when stabilized to preserve the sulfhydryl form of cysteine, for example, by reaction with iodoacetamide, the compounds of the invention also include linearized forms which are stabilized with suitable reagents. As defined herein, "SH-stabilized" forms of the peptides of the invention contain sulfhydryl groups reacted with standard reagents to prevent reformation into disulfide linkages.

The peptides of the invention may contain 1–2 amino acid residues in the D, rather than in the native L form.

The amino acid notations used herein are conventional and are as follows:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript ($^\dagger$).

The basic residues noted by $B_i$ have a positive charge due to association with H ion at physiological pH and the residue is attracted by aqueous solution so as to seek the surface positions in the conformation of a peptide in which it is contained when the peptide is in aqueous medium at physiological pH.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

The gene-encoded basic amino acids are arginine, lysine and histidine.

Non-gene encoded basic amino acids include ornithine (Orn) and homoarginine (Har).

Other basic amino acid substitutions of those encoded in the gene can also be included in peptide compounds within the scope of the invention and can be classified within this general scheme according to their structure.

In all of the peptides of the invention, one or more amide linkages (—CO—NH—) may optionally be replaced with another linkage which is an isostere such as $—CH_2NH—$, $—CH_2S—$, $—CH_2CH_2$, —CH=CH— (cis and trans), $—COCH_2—$, $—CH(OH)CH_2—$ and $—CH_2SO—$. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 ($—CH_2NH—$, $—CH_2CH_2—$); Spatola, A. F., et al., *Life Sci* (1986) 38:1243–1249 ($—CH_2—S$); Hann, M. M., *J Chem Soc Perkin Trans I* (1982) 307–314 (—CH—CH—, cis and trans); Almquist, R. G., et al., *J Med Chem* (1980) 23:1392–1398 ($—COCH_2—$); Jennings-White, C., et al., *Tetrahedron Lett* (1982) 23:2533 ($—COCH_2—$); Szelke, M., et al., European Application EP 45665 (1982) CA:97:39405 (1982) ($—CH(OH) CH_2—$); Holladay, M. W., et al., *Tetrahedron Lett* (1983) 24:4401–4404 ($—C(OH) CH_2—$); and Hruby, V. J., *Life Sci* (1982) 31:189–199 ($—CH_2—S—$).

In an alternative embodiment, the peptides of the invention are defined as described by formula (1) or (2), but wherein the specific peptide in each case is determined by the isolatability of the peptide from avian neutrophils by the invention method. The invention method comprises the steps of providing an ultrafiltrate of a lysate of avian neutrophils and isolating antimicrobial peptides of about 35–40 amino acids. These peptides can further be defined by the ability of DNA encoding them to hybridize under stringent conditions to DNA encoding the peptides exemplified as Gal1, Gal1α or Gal2 herein.

Particularly preferred compounds of the invention are:

Gal 1α GRKSDCFRKNGFCAFLKCPYLTLISGKCSRFHLCCKRIW (SEQ ID NO: 3)

Gal 1 GRKSDCFRKS GFCAFLKCPSLTLISGKCSRFYLCCKRIW (SEQ ID NO: 4)

both the linear and cyclic forms thereof, and including the N-terminal acylated and C-terminal amidated forms; and Gal 2 LFCKGGSCHFGGCPSHLIKVGSCFGFRSCCKWPWNA (SEQ ID NO: 5)

both the linear and cyclic forms thereof, and including the N-terminal acylated and C-terminal amidated forms.

These preferred compounds are related to the β-defensins, as shown in FIG. 1.

Preparation of the Invention Compounds

The invention compounds, often designated herein "gallinacins" are essentially peptide backbones which may be modified at the N- or C-terminus and also may contain one or two cystine disulfide linkages. The peptides may first be synthesized in noncyclized form. These peptides may then be converted to the cyclic peptides if desired by standard methods of cystine bond formation. As applied to the gallinacins herein, "cyclic forms" refers to those forms which contain cyclic portions by virtue of the formation of disulfide linkages between cysteine residues in the peptide. If the straight-chain forms are preferred, it is preferable to stabilize the sulfhydryl groups for any peptides of the invention which contain two or more cysteine residues.

Standard methods of synthesis of peptides the size of gallinacins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1-6C) as defined above. Similarly, the carboxy terminus may be amidated so as to have the formula $—CONH_2$, —CONHR, or $—CONR_2$, wherein each R is independently hydrocarbyl (1-6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

Formation of disulfide linkages, if desired, is conducted in the presence of mild oxidizing agents. Chemical oxidizing agents may be used, or the compounds may simply be exposed to the oxygen of the air to effect these linkages.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host. Alternatively, although less convenient, the DNA can be obtained, at least initially, by screening a cDNA library prepared from chicken neutrophils using probes or PCR primers based on the sequences of the gallinacins described herein. This results in recovery of the naturally occurring sequence encoding the gallinacins of the invention. Obtention of this native sequence is significant for purposes other than the synthesis of the gallinacins per se; the availability of the naturally occurring sequences provides a useful probe to obtain corresponding DNA encoding gallinacins of other species. Thus, cDNA libraries, for example, of leukocytes derived from other animals can be screened using the native DNA, preferably under conditions of high stringency. High stringency is as defined by Maniatis, et al. *Molecular Cloning: a Laboratory Manual* 2nd Ed, Cold Spring Harbor Laboratory Press (1989), the relevant portions of which are incorporated herein by reference. This procedure also permits recovery of allelic variants of these peptides from the same species.

Alternatively, the gallinacins can be prepared by isolation from neutrophils of an avian species using techniques similar to those disclosed herein for the isolation of porcine gallinacins. In general, these techniques involve preparing a lysate of a neutrophil preparation, ultrafiltering the supernatant of the clarified lysate and recovering the ultrafiltrate. The ultrafiltrate is then subjected to chromatographic separation. The location of fragments having antimicrobial activity corresponding to gallinacins can be assessed using criteria of molecular weight and assaying the fractions for the desired activities as described herein. The native forms of these peptides are believed to be the cyclic forms; if desired, the linearized forms can be prepared by treating the peptides with reducing agents and stabilizing the sulfhydryl groups that result.

Isolated and recombinantly produced forms of the gallinacins may require subsequent derivatization to modify the N- and/or C-terminus and, depending on the isolation procedure, to effect the formation of cystine bonds as described hereinabove. Depending on the host organism used for recombinant production and the animal source from which the protein is isolated, some or all of these conversions may already have been effected.

For recombinant production, the DNA encoding the gallinacins of the invention is included in an expression system which places these coding sequences under control of a suitable promoter and other control sequences compatible with an intended host cell. Types of host cells available span almost the entire range of the plant and animal kingdoms. Thus, the gallinacins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-á-vis these infective agents.

The gallinacins of the invention can be produced in a form that will result in their secretion from the host cell by fusing to the DNA encoding the gallinacin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the gallinacins of the invention can be produced in a variety of modalities including chemical synthesis, recombinant production, isolation from natural sources, or some combination of these techniques.

Those members of the gallinacin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the gallinacins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The gallinacins of the invention in immunogenic form are then injected into a suitable mammalian host and antibody titers in the serum are monitored. Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

The antibodies of the invention are, of course, useful in immunoassays for determining the amount or presence of the gallinacins. Such assays are essential in quality controlled production of compositions containing the gallinacins of the invention. In addition, the antibodies can be used to assess the efficacy of recombinant production of the gallinacins, as well as screening expression libraries for the presence of gallinacin encoding genes.

Compositions Containing the Gallinacins and Methods of Use

The gallinacins of the invention are effective in inactivating a wide range of microbial targets, including gram-positive and gram-negative bacteria and yeast. Accordingly, they can be used in disinfectant compositions and as preservatives for materials such as foodstuffs, cosmetics, medicaments, or other materials containing nutrients for organisms. For use in such contexts, the gallinacins are supplied either as a single gallinacin, in admixture with several other gallinacins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays.

For use as antimicrobials for treatment of animal subjects, the gallinacins of the invention can be formulated as pharmaceutical or veterinary compositions. Depending on the subject to be treated, the mode of administration, and the type of treatment desired—e.g., prevention, prophylaxis, therapy; the gallinacins are formulated in ways consonant with these parameters. A summary of such techniques is found in Remington's *Pharmaceutical Sciences,* latest edition, Mack Publishing Co., Easton, Pa.

The gallinacins of the invention can be administered singly or as mixtures of several gallinacins or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The gallinacins can be administered also in liposomal compositions or as microemulsions.

If administration is to be oral, the gallinacins of the invention must be protected from degradation in the stomach using a suitable enteric coating. This may be avoided to some extent by utilizing amino acids in the D-configuration, thus providing resistance to proteases. However, the peptide is still susceptible to hydrolysis due to the acidic conditions of the stomach; thus, some degree of enteric coating may still be required.

The gallinacins of the invention may also be applied to plants or to their environment to prevent microbial-induced diseases in these plants. Suitable compositions for this use will typically contain a diluent as well as a spreading agent or other ancillary agreements beneficial to the plant or to the environment.

Thus, the gallinacins of the invention may be used in any context wherein an antimicrobial action is required. This use may be an entirely in vitro use, or the peptides may be administered to organisms.

In addition, the antimicrobial activity may be generated in situ by administering an expression system suitable for the production of the gallinacins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The following examples are intended to illustrate but not to limit the invention.

EXAMPLE 1

Isolation of Gal1, Gal1α and Gal2

Cross Broiler-6 strain chickens, 60–80 days old, were injected intraperitoneally with 200 ml of normal saline solution that contained 0.5% starch. After 68 hours, the birds were sacrificed and their peritoneal cavities were lavaged with 100–200 ml of normal saline that contained 5 I.U. of heparin/ml. The recovered cell suspensions were centrifuged at 250×g for 10 min at 4° C. and the cell pellets were subjected to hypotonic lysis in ice-cold distilled water to remove associated erythrocytes. Approximately $4.5\times10^9$ cells (95% neutrophils) were recovered from 30 chickens. The cells were homogenized in 40 ml of ice cold 10% HOAc, stirred for 2 hr at 4° C., and then centrifuged. The sediment was reextracted twice more in this manner, and all of the supernatants were pooled and concentrated by vacuum centrifugation (Speed Vac Concentrator, Savant Instruments, Hicksville, N.Y.).

The lyophilized acid extract was dissolved in 20 ml of 5% HOAc and chromatographed on a 4.0×70 cm column of Acrilex P10 (Reanal, Hungary) that was previously equilibrated with 5% HOAc. The peptides of interest eluted at an elution volume slightly larger than the column's bed volume and were initially detected by acid urea gel electrophoresis (AU-PAGE).

FIG. 2 shows the elution pattern. The fractions subject to further purification are indicated by the hatched area, and contained a mixture of low molecular weight cationic peptides, some of which were disulfide-rich, as judged by their altered migration or disappearance of bands on AU-PAGE gels following performic acid oxidation.

Assay Method

Aliquots of these column fractions were dried by vacuum centrifugation, resuspended in a small volume (approximately 17 μl) of 0.01% HOAc and 5 μl samples were tested for antimicrobial activity against *Escherichia coli* ML-35, *Listeria monocytogenes* strain EGD and *Candida albicans* strain 820, by the ultrasensitive radial diffusion technique described by Lehrer, R. I. et al. *J Immunol Meth* (1991) 137:167–173. The underlay agars used for all organisms had a final pH of 7.4 and contained 10 mM buffer (9 mM sodium phosphate, 1 mM sodium citrate), 1% w/v agarose and 0.30 mg/ml of trypticase soy broth powder (BBL, Cockeysville, Md.). A 1 mm diameter clear zone around the sample well after overnight incubation corresponded to 10 units of microbicidal activity.

Figure 3A:
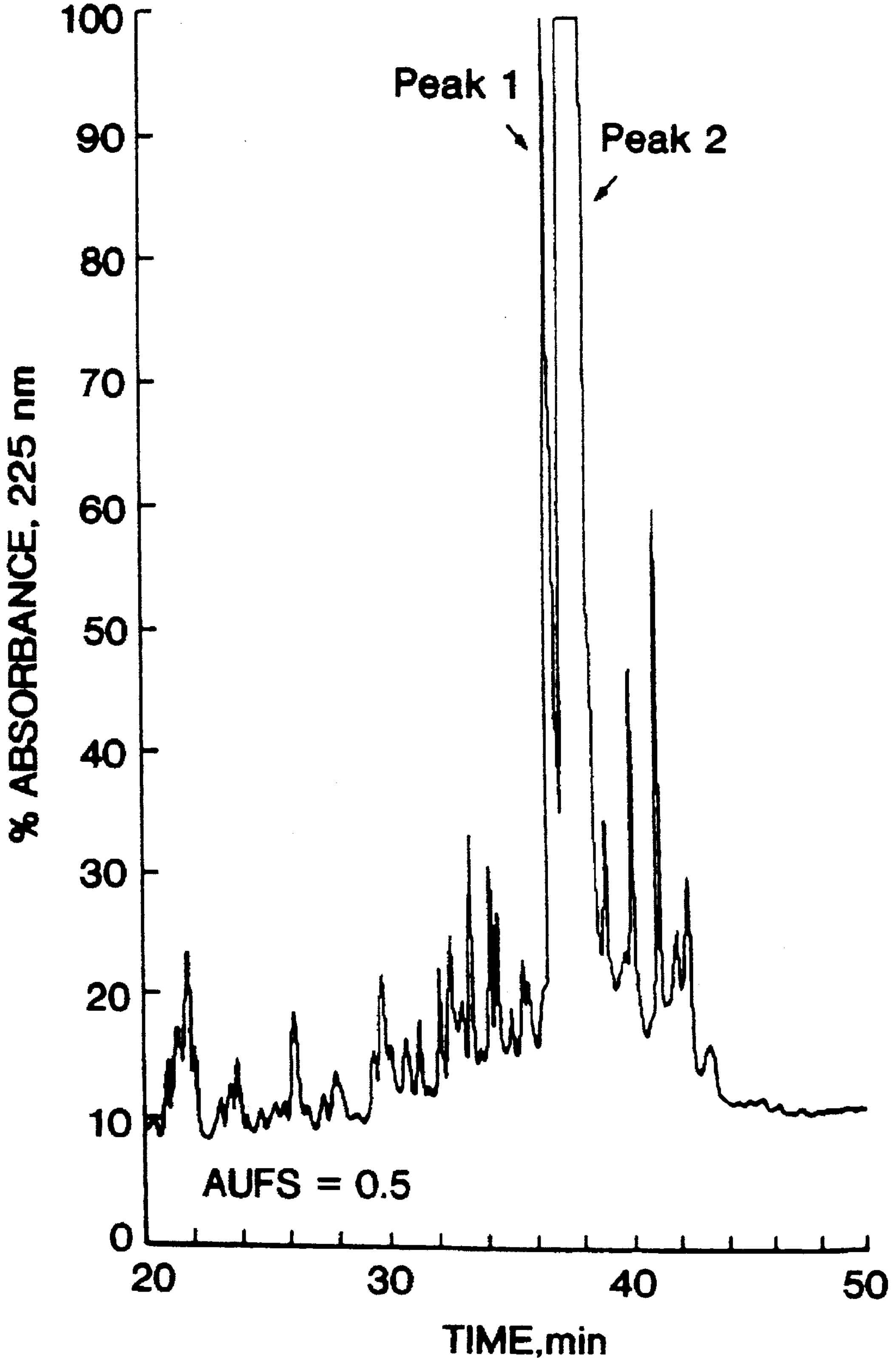
FIGS. 3*a* and 3*b* show an elution pattern obtained when fractions from the Acrilex P10 column of FIG. 2 is applied to HPLC.
Figure 3B:
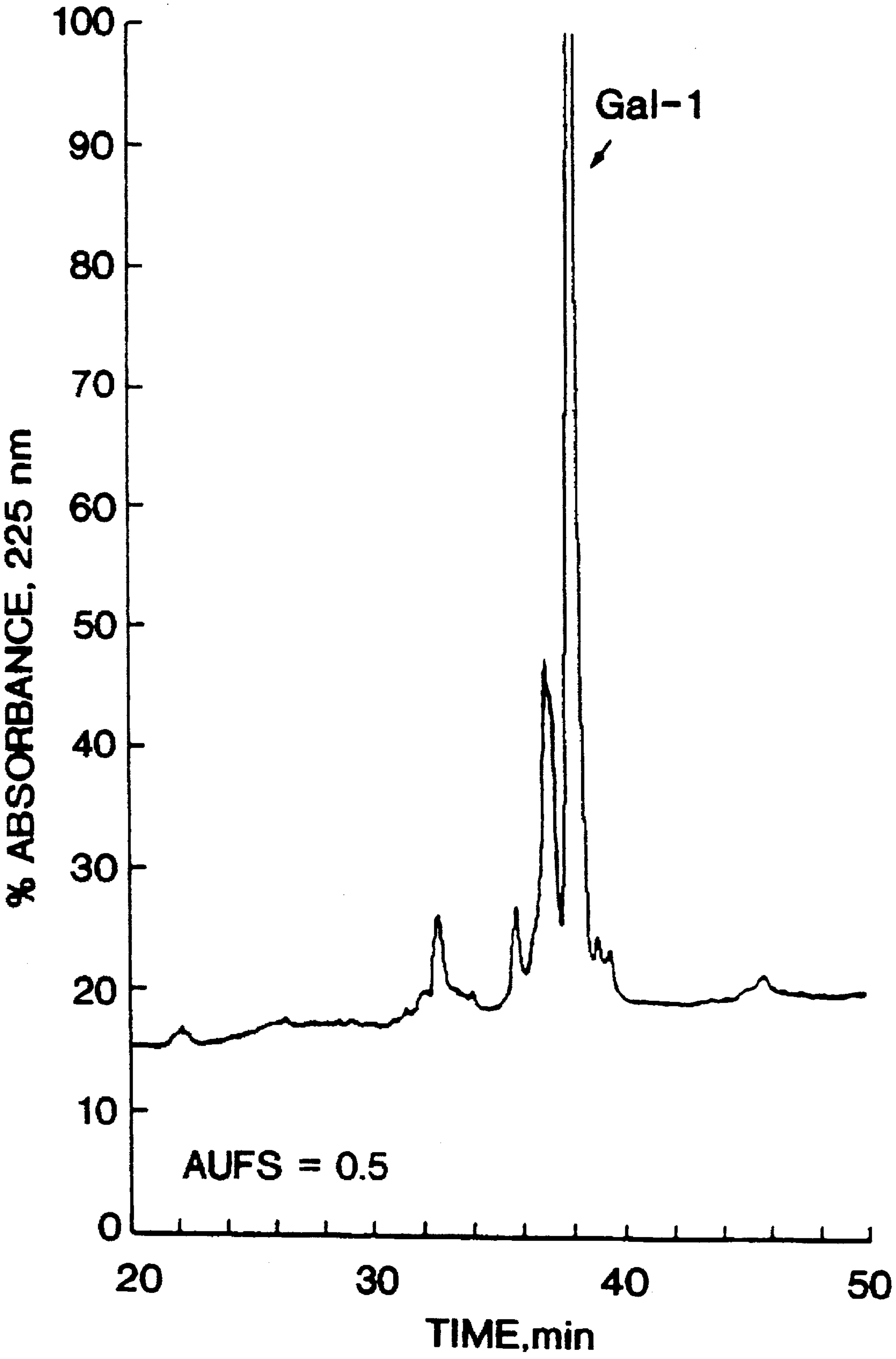
Figure 4A:
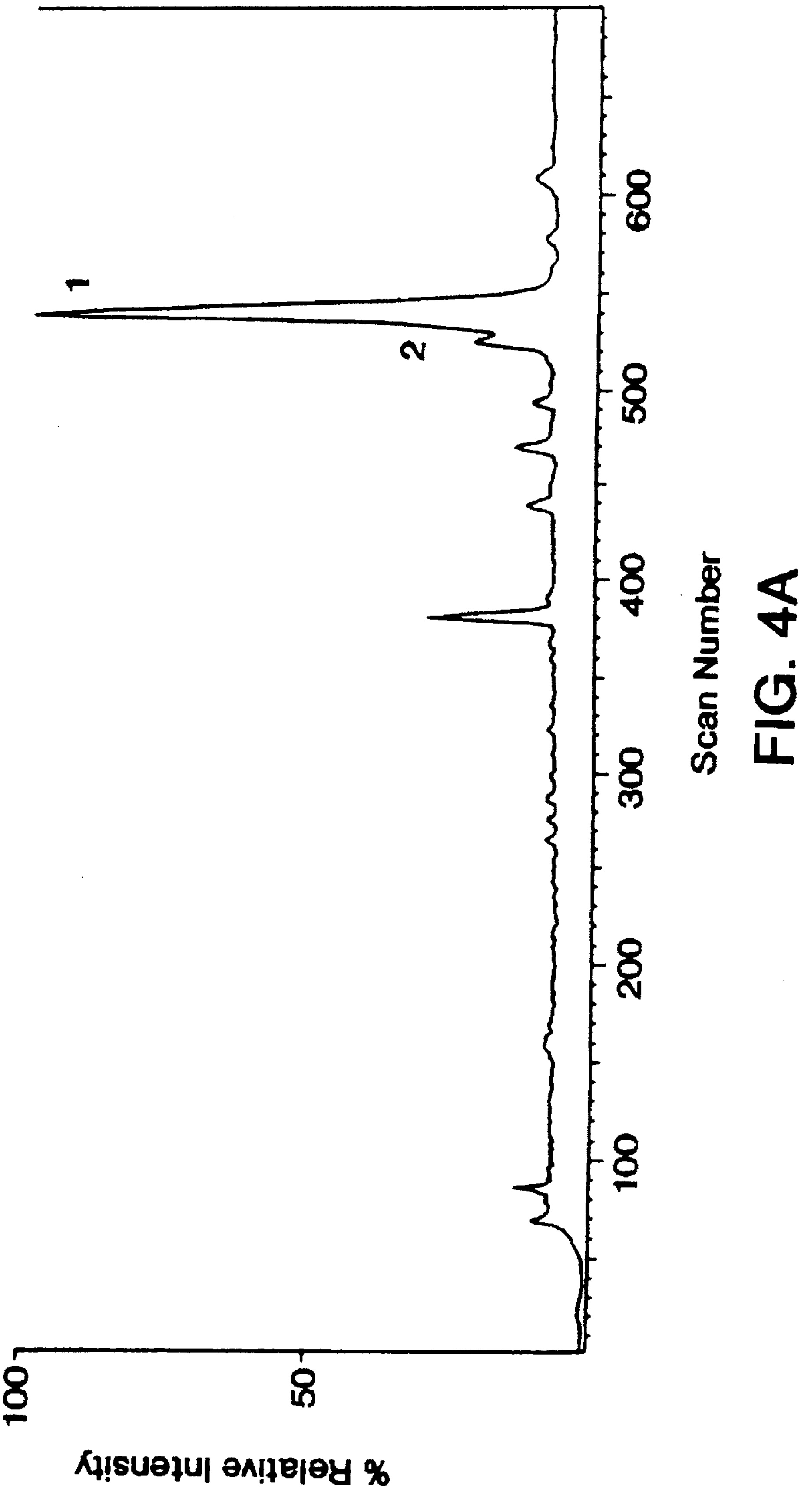
FIGS. 4*a*–4*e* show the results of mass spectral sequence determination.
Figure 4B:
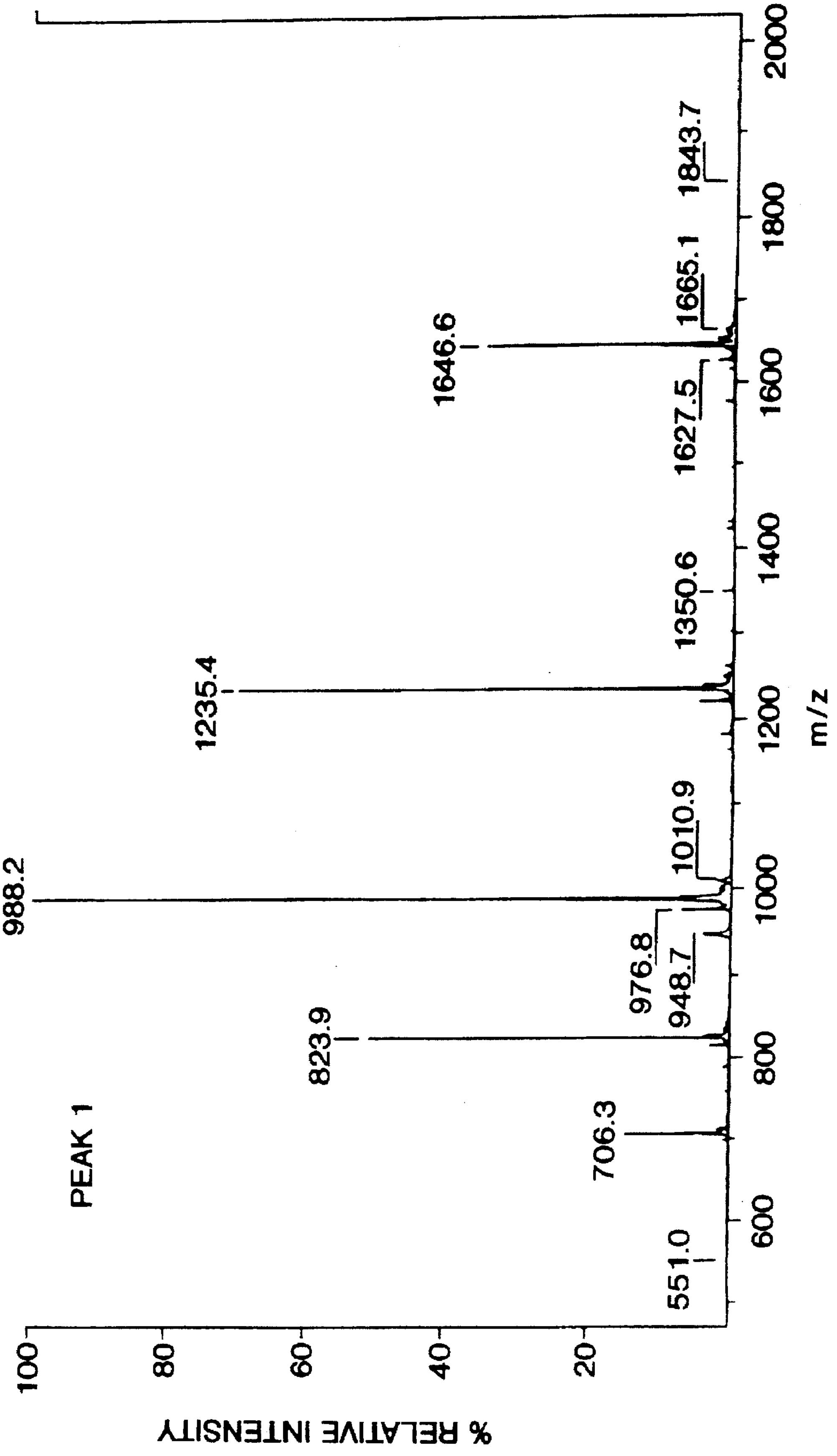
Figure 4C:
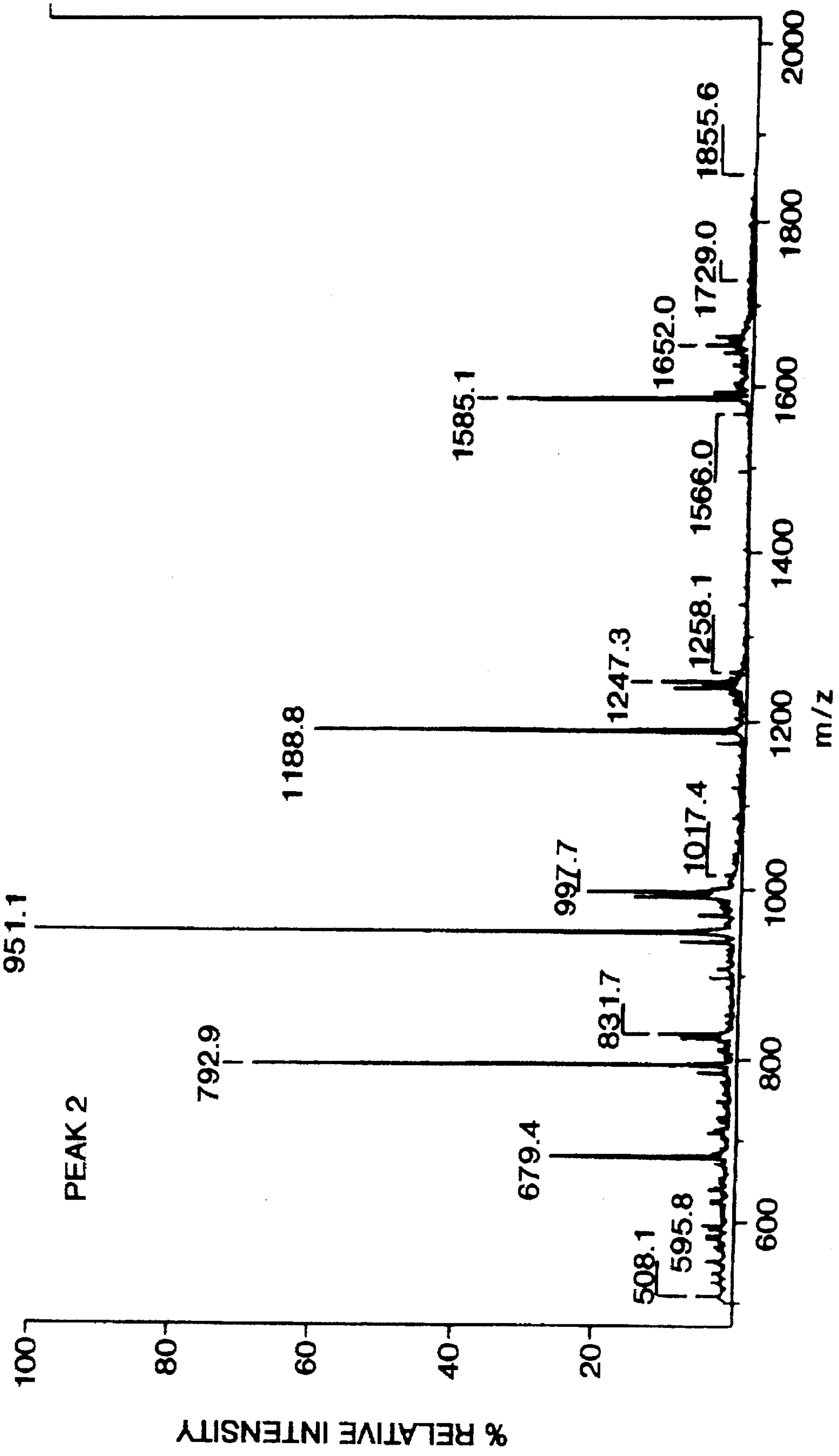
Figure 4D:
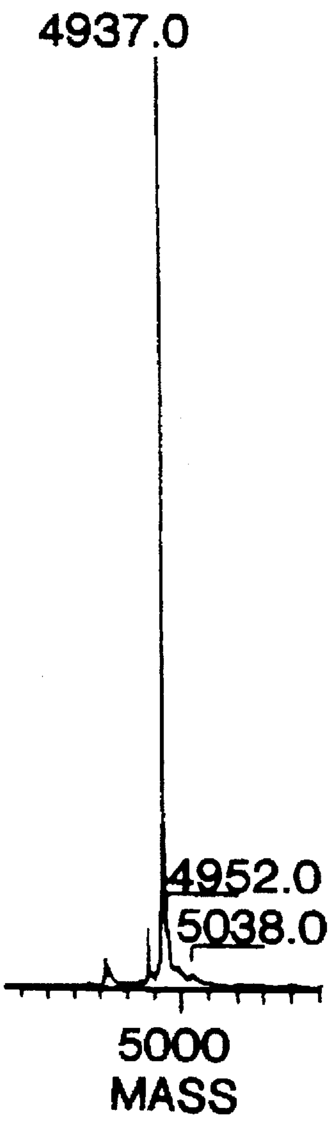
Figure 4E:
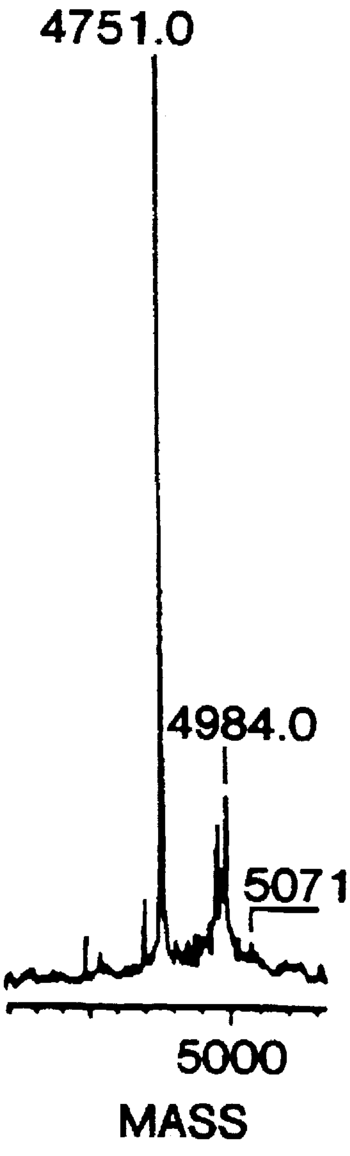
Figure 5A:
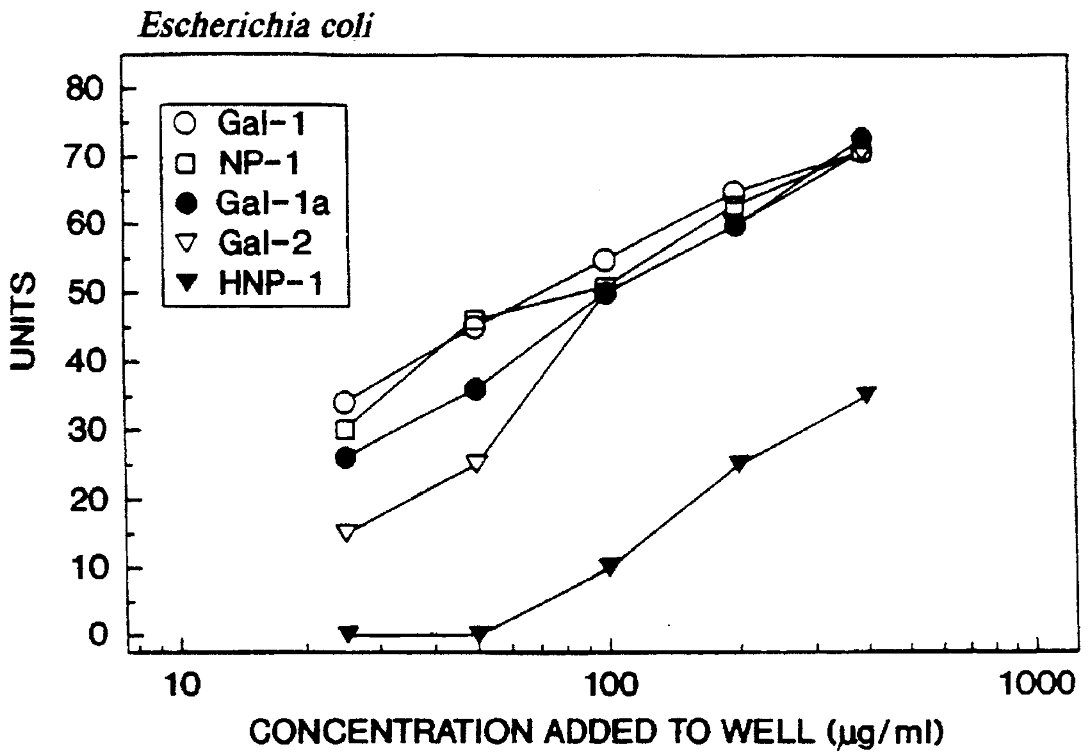
FIG. 5*a* shows antibacterial activity of Gal1, Gal1α and Gal2 against *E. Coli;*
Figure 5B:
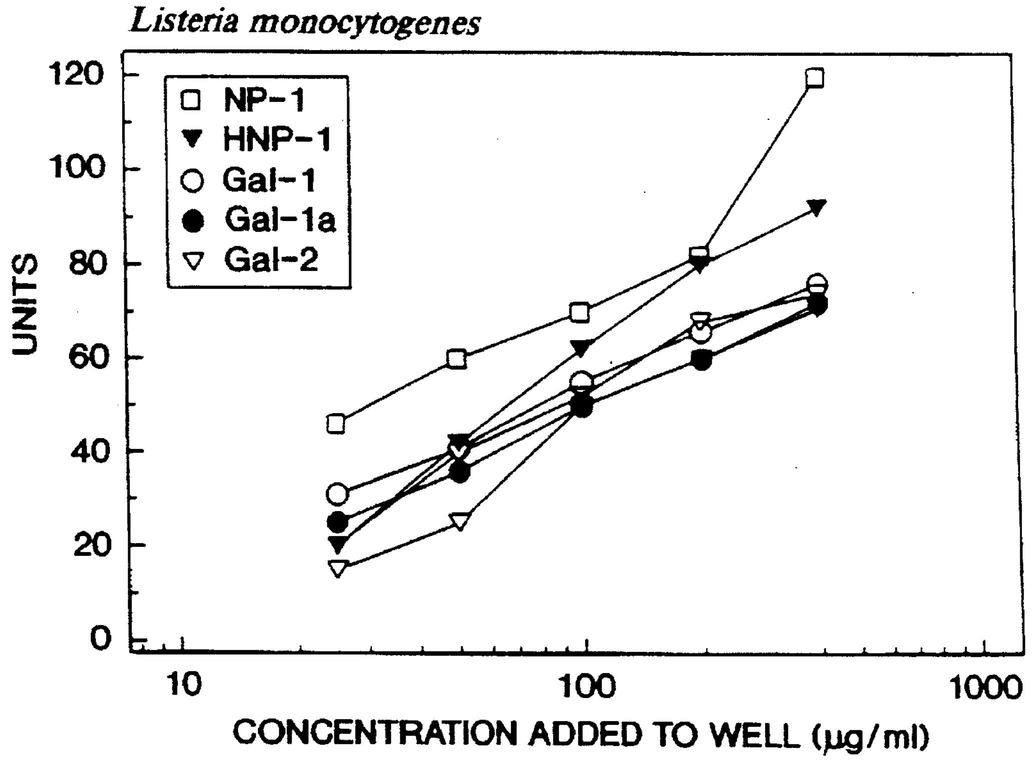
FIG. 5*b* shows antibacterial activity of Gal1, Gal1α and Gal2 against *Listaria monocytogenes;*
Figure 5C:
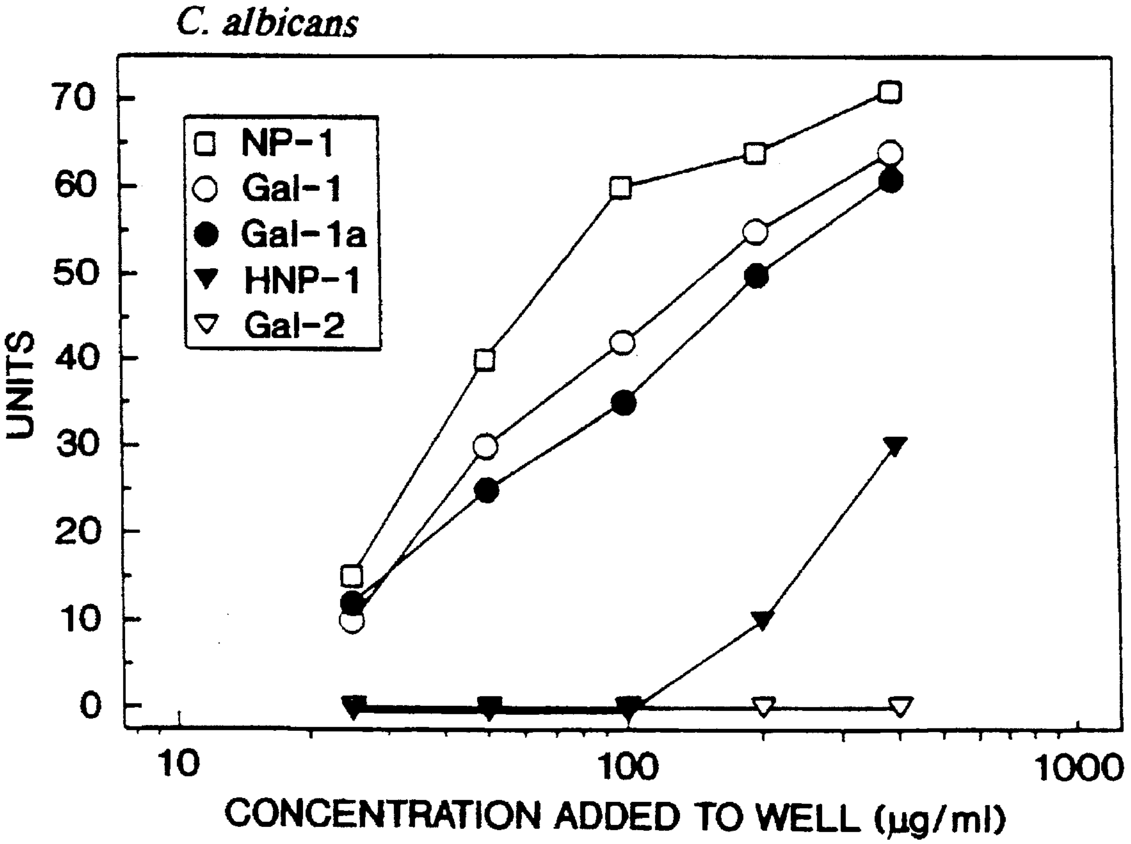
FIG. 5*c* shows antifungal activity of Gal1, Gal1α and Gal2 against *Candida albicans.*

The fractions containing antimicrobial activity (shown hatched in FIG. 2) were pooled, concentrated and subjected to HPLC purification on a 4.6×250 mm Vydac C-18 column (The Separations Group, Hesperia, Calif.) using a linear gradient of $H_2O$ and acetonitrile that contained 0.1% TFA. As shown in FIG. 3*a*, the gallinacins emerged as two distinct peaks between 36–40% acetonitrile. Gallinacin-1 (peak 1) was further purified by recycling it through the same column with a slower acetonitrile gradient that used 0.13% HFBA as an ion pairing agent (FIG. 3*b*). Gallinacins 1α and 2 (accompanied by Gal3[1]) emerged from the initial RP-HPLC purification in peak 2. The components of peak 2 were resolved by AU-PAGE, followed by a final step of RP-HPLC purification. The purified gallinacins were homogeneous by Coomassie-stained AU-PAGE and silver-stained Tricine-SDS-PAGE with a Bio-Rad Prep Cell 491 (Bio-Rad, Hercules, Calif.) and a 10 cm high, 12.5% acid urea gel column, as previously described by Harwig, S. S. L. et al. *Anal biochem* (1993) 208:382–386, followed by reversed-phase HPLC on the Vydac C-18 column.

[1]Gallinacin 3, which was N-terminally blocked, is not described further herein.

EXAMPLE 2

Characterization of the Gallinacins

The purified gallinacins were characterized by composition analysis, sequence determination, endoprotease mapping of carboxymethylated (CM) gallinacins using ArgC, LysC and trypsin and by carboxyl-terminal sequence determination by conventional amino acid analysis of residues released by carboxypeptidase-Y. Since our amounts of purified Gal1 and Gal1α were very limited and carboxypeptidase-Y digestion was inefficient, we adopted another approach—"on-line" mass analysis—to ascertain carboxyl-terminal amino acid sequences as follows:

Approximately 200 pmol each of CM-Gal1 or Gal1α was resuspended in 8 μl of 0.1M $NH_4OAc$, pH 6.2 and incubated at 37° C. for 10 minutes. An aliquot of carboxypeptidase-Y was added so the final enzyme/substrate ratio was 1/75 by mass. Aliquotes were removed after 3 min, 5 min and 40 min, and the reaction was terminated by adding glacial HOAc (25% v/v final concentration) and frozen for subsequent LC-MS analysis. A total amount of 3 nmol of CM-gal-2 was digested with carboxypeptidase-Y under the same conditions, aliquots were removed at 1.5 min, 3 min, 5 min and 10 min and the released amino acid(s) were determined as phenylthiocarbamyl derivative(s) following derivatization of the reaction mixture.

The greatest challenges involved placement of the carboxyl-terminal residues. Identification of Ala and Asn in Gal2 was accomplished conventionally by the kinetic measurement of amino acid(s) released by carboxypeptidase-Y. The third residue, Trp, was placed by mass measurement of the C-terminal tryptic fragment. Since residues at positions 32 (Trp) and 33 (Pro) (the numbering system corresponds to that in FIG. 1) had already been established by two independent sequence runs, the mass value of 673.3 obtained for this fragment indicated that another Trp was the only possible fit at position 34. (Note that position 34 of Gal2 corresponds to residue 37 of Gal1α, which was used to establish the numbering scheme shown in FIG. 1.) The presence of two tryptophan residues in Gal2 sequence was further confirmed by spectrophotometric measurement.

The placement of carboxyl-terminal tryptophan in Gal1α and Gal1 was accomplished by "on-line" LC-Electrospray-Mas-Spectrometric analysis of carboxypeptidase-Y digestion mixtures at various time intervals.

Mass spectrometric analyses were performed at Beckman Research Institute of City of Hope (Duarte, Calif.) on a triple quadrupole TSQ-700 mass spectrometer (Finnigan-MAT, San Jose, Calif.) equipped with an electrospray ion source operating at atmospheric pressure. Mass spectra were recorded in the positive ion mode. A sheath flow of 2-methoxyethanol at a flow rate equal to the flow rate coming from the micro capillary HPLC system was used for all LC-MS experiments. The microcapillary HPLC system, constructed at the City of Hope, consisted of a fused silica column with an inner diameter of 250 μm packed with Vydac 3 μm C18 RP support. A detailed description of the design and operation was reported recently by Harwig, S. S. L. et al. in *Techniques for Protein Chemistry V* (Crabbe, J. ed.) (1994) in press; Swiderek, K. M. et al. (ibid.). Mass scans were continually acquired every three seconds in a mass range from 500–2000 and the data collection was monitored using both the base peak (representing the highest intensity per scan) and the reconstructed ion current profile (representing the continuous collection of the total ion current per scan). Spectra were generated by averaging the scans containing the peak, and the mass assignments were made using the Finnigan MAT BIOMASS data reduction software.

The results of one such analysis are shown in FIG. 4. As indicated by the reconstructed ion current profile (FIG. 4*a*), several peaks were obtained when 50 pmol of the 3 min carboxypeptidase digestion mixture of CM-Gal1α were subjected to LC-MS. The corresponding mass spectra of the major peak (marked #1) and the peak immediately preceding it (marked #2) are shown in FIGS. 4*b* 4*e*. The average masses for these two peaks (shown in the insets) derived from these spectra were 4937.0 and 4751.0, respectively. The first value corresponds to the undigested CM-Gal1α mass value. The second value, 186 mass units less than that of the undigested peptide, is consistent only with tryptophan being the carboxyl-terminal residue. A similar mass difference was observed with carboxypeptidase digestion studies of CM-Gal1.

The placement of tryptophan was also confirmed by spectrophotometric measurements of solutions of Gal1α and Gal1 whose concentrations were established by amino acid analysis using norleucine as internal standard.

The calculated average mass values of native Gal1α, Gal1 and Gal2, given that the 6 half-cysteines are linked in three intramolecular disulfide bonds, are 4581.51, 4504.43 and 3915.58. The respective ESI-MS measurement yielded average mass values of 4582.0, 4505.0 and 3916.0, all of which are consistent with the expected values.

The three gallinacins sequenced and their relationship to the known defensins is shown in FIG. 1. As shown in FIG. 1, Gal1α and Gal1 differed only in three positions, $Ans^{10}$/$Ser^{10}$, $Tyr^{20}$/$Ser^{20}$ and $His^{32}$/$Tyr^{32}$. The additional positive charge resulting from the difference at residue 32 is consistent with Gal1α migrating slightly in advance of Gal1 in AU-PAGE gels. Gal2 (36 residues) was identical to Gal1 (39 residues) in 15 of its 36 residues (41.7%), notwithstanding its 3 residue N-terminal truncation and 2 residue C-terminal elongation relative to Gal1. Gal2 also differed from Gal1 and Gal1α by having only four residues, instead of six, between its first and second cysteines. The overall effect of these truncations was to delete three positively charged residues from the amino terminus of Gal2, perhaps accounting for its relatively poor activity, compared to Gal1 and Gal1α, against *C. albicans*.

Alignment of gallinacin sequences with bovine tracheal antimicrobial peptide ("TAP") and several bovine neutrophil β-defensins (BNBD), showed homology involving all six conserved cysteine residues as well as three other residues ($Gly^{11}$, $Pro^{19}$ and $Gly^{26}$) as shown in FIG. 1. The spacing of the gallinacin cysteine residues was virtually identical to that of β-defensins, but distinct from that of classical defensins.

EXAMPLE 3

Antimicrobial Activity

The radial diffusion assay in agarose gels described in Example 1 was also used to test the activity of the purified gallinacins. FIGS. *5a*, *5b* and *5c* show the results against three test organisms in units described as above. Rabbit defensin (NP-1) and human defensin (HNP-1) were used as controls.

FIG. *5a* shows that the gallinacins are comparably effective against *E. coli* ML-35P with respect to NP-1, and more effective than HNP-1. The gallinacins were also effective against *Listeria monocytogenes,* strain EGD as shown in FIG. *5b*. In FIG. *5c*, Gal1 and Gal1α were also shown effective against *Candida albicans;* Gal2 was not. In general, these peptides are approximately as effective as rabbit defensin NP-1 on a weight basis and are more effective than HNP-1.

We claim:

1. A purified and isolated compound of the formula 1 2 3 4 5 6 7 8 9 10
G—$B_2$—$B_3$—S—(D/E)—C—F—$B_8$—$B_9$—(N/S)—
11 12 13 14 15 16 17 18 19 20
G—F—C—(G/A/S)—F—(V/L/I)—$B_{17}$—C—P—(Y/S)—
21 22 23 24 25 26 27
(V/L/I)—T—(V/L/I)—(V/L/I)—(G/A/S)—G—$B_{27}$—
28 29 30 31 32 33 34 35 36
C—(G/A/S)—$B_{30}$—F—(H/Y)—(V/L/I)—C—C—$B_{36}$—
37 38 39
$B_{37}$—I—W (1)

SEQ ID NO. 1 wherein each $B_i$ represents a basic amino acid, and the N-terminal acylated and C-terminal amidated or esterified forms thereof, which is either in the optionally —SH stabilized linear or in the cystine-bridged form.

2. The compound of claim 1 which contains 3 cystine bridges.

3. The compound of claim 1 which is in the linear form.

4. The compound of claim 1 wherein the C-terminal carboxyl is of the formula selected from the group consisting of COOH or the salts thereof; COOR, $CONH_2$, CONHR, and $CONR_2$ wherein each R is independently hydrocarbyl (1-6C).

5. The compound of claim 1 wherein the amino group at the N-terminus is of the formula $NH_2$ or NHCOR wherein R is hydrocarbyl(1-6C).

6. The compound of claim 1 wherein each or $B_2$, $B_3$, $B_8$, $B_9$, $B_{17}$, $B_{27}$, $B_{30}$, $B_{36}$ and $B_{37}$ is independently selected from the group consisting of R, K and homoarginine.

7. The compound of claim 1 wherein each of $B_3$, $B_9$, $B_{17}$, $B_{27}$ and $B_{36}$ is K.

8. The compound of claim 1 which is selected from the group consisting of

Gal 1 GRKSDCFRKSGFCAFLKCPSLTLISGKCSRFYLCCKRIW (SEQ ID NO: 3)

and

Gal 1α GRKSDCFRKNGFCAFLKCPYLTLISGKCSRFHLCCKRIW (SEQ ID NO: 4)

and the amidated forms thereof either in linear or cystine-bridged form.

9. A purified and isolated compound of the formula:

$$\left.\begin{array}{l}
1\ \ 2\ \ 3\ \ 4\ \ 5\ \ 6\ \ 7\ \ 8\ \ 9\ \ 10 \\
G-B_2-B_3-S-(D/E)-C-F-B_8-B_9-(N/S)- \\
11\ \ 12\ \ 13\ \ 14\ \ 15\ \ 16\ \ 17\ \ 18\ \ 19\ \ 20 \\
G-F-C-(G/A/S)-F-(V/L/I)-B_{17}-C-P-(Y/S)- \\
21\ \ 22\ \ 23\ \ 24\ \ 25\ \ 26\ \ 27 \\
(V/L/I)-T-(V/L/I)-(V/L/I)-(G/A/S)-G-B_{27}- \\
28\ \ 29\ \ 30\ \ 31\ \ 32\ \ 33\ \ 34\ \ 35\ \ 36 \\
C-(G/A/S)-B_{30}-F-(H/Y)-(V/L/I)-C-C-B_{36}- \\
37\ \ 38\ \ 39 \\
B_{37}-I-W
\end{array}\right\} \quad (1)$$

SEQ ID NO. 1 and the N-terminal acylated, C-terminal amidated or esterified forms thereof in either the linearized or the cystine-bridged form wherein each $B_i$ is independently a basic amino acid residue at the designated position and wherein said cysteine-bridged compound is isolatable from the neutrophils of an avian subject by a process which comprises subjecting the ultrafiltrate of a lysate of said neutrophils to chromatographic separation techniques to obtain a fraction containing compounds of formula (1) and recovering said compounds of formula (1).

* * * * *